United States Patent [19]

Parg et al.

[11] 4,321,371
[45] Mar. 23, 1982

[54] SUBSTITUTED N-BENZOYLANTHRANILIC ACID DERIVATIVES AND THEIR ANHYDRO COMPOUNDS

[75] Inventors: Adolf Parg, Bad Durkheim; Bruno Wuerzer, Otterstadt; Gerhard Hamprecht, Weinheim, all of Fed. Rep. of Germany

[73] Assignee: BASF Aktiengesellschaft, Fed. Rep. of Germany

[21] Appl. No.: 178,677

[22] Filed: Aug. 15, 1980

[30] Foreign Application Priority Data

Aug. 27, 1979 [DE] Fed. Rep. of Germany ....... 2934543

[51] Int. Cl.³ .................. C07D 265/12; C07C 79/46; C07D 211/86; C07D 213/62
[52] U.S. Cl. ........................................ 544/92; 560/21; 548/129; 546/277; 546/297; 546/300; 544/238; 260/465 D; 564/156
[58] Field of Search .................. 560/21; 548/129; 546/277, 297, 300; 544/238, 92; 260/465 D; 564/156

[56] References Cited

U.S. PATENT DOCUMENTS

| | | | |
|---|---|---|---|
| 2,232,736 | 2/1941 | Schulze | 544/92 |
| 3,232,736 | 2/1966 | Seefelder et al. | 544/92 |
| 3,914,121 | 10/1975 | Doyle | 544/92 |
| 3,970,652 | 7/1976 | Doyle | 544/92 |
| 4,116,953 | 9/1978 | Dimroth et al. | 544/92 |

FOREIGN PATENT DOCUMENTS

| | | | |
|---|---|---|---|
| 1191171 | 9/1962 | Fed. Rep. of Germany | 544/92 |
| 1373264 | 9/1962 | France | 544/92 |

Primary Examiner—John M. Ford
Assistant Examiner—Robert C. Whittenbaugh
Attorney, Agent, or Firm—Keil & Witherspoon

[57] ABSTRACT

Substituted N-benzoylanthranilic acid derivatives of the formula I

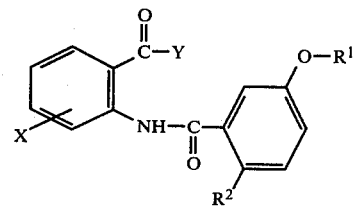

and their anhydro compounds, of the formula II

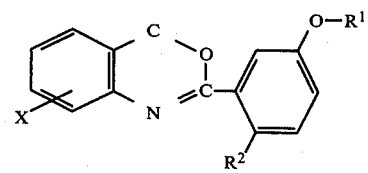

where
$R^1$ is substituted phenyl,
$R^2$ is hydrogen, nitro, cyano or halogen,
X is hydrogen, halogen, nitro or cyano, or is alkyl, haloalkyl, alkoxy, haloalkoxy, haloalkylmercapto or alkylmercapto, each of 1 to 4 carbon atoms, and
Y is $-OR^6$ or

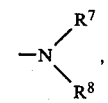

where
$R^6$ is hydrogen, or is alkyl, alkenyl or alkynyl each of up to 4 carbon atoms, or is one equivalent of an alkaline earth metal cation, of an alkali metal cation or of an ammonium ion which is unsubstituted or is substituted by alkyls of 1 to 4 carbon atoms, and
$R^7$ and $R^8$ independently of one another are hydrogen or alkyl of 1 to 4 carbon atoms, herbicides containing these compounds, and processes for controlling undesired plant growth by means of these compounds.

7 Claims, No Drawings

SUBSTITUTED N-BENZOYLANTHRANILIC ACID DERIVATIVES AND THEIR ANHYDRO COMPOUNDS

The present invention relates to substituted N-benzoylanthranilic acid derivatives and their anhydro compounds, to processes for their preparation, to herbicides which contain these compounds as active ingredients, and to processes for controlling undesired plant growth by means of these compounds.

German Pat. No. 1,191,171 and French Pat. No. 1,373,264 disclose that N-benzoylanthranilic acid and its anhydro compound, and derivatives, substituted in the benzoyl radical, of the said acid and anhydro compound, are herbicidally active. The Examples illustrating this action show that in the case of unsubstituted N-benzoylanthranilic acid and its anhydro compound relatively high doses are required and only a very limited number of species of undesired plants can be controlled. The compounds are well tolerated by monocotyledonous and dicotyledonous crop plants.

A number of substituted anhydro compounds, ie. 4H-3,1-benzoxazin-4-ones, carrying a substituted phenyl radical in the 2-position, are described, in U.S. Pat. Nos. 3,914,121 and 3,970,652, as being non-phytotoxic or as being useless as herbicides because of the large amounts required to produce an effect.

U.S. Pat. Nos. 3,914,121 and 3,970,652 single out a range of 2-aryl-4H-3,1-benzoxazin-4-one derivatives, eg. 2-(m-trifluoromethyl-phenyl)-4H-3,1-benzoxazin-4-one, as particularly useful for controlling undesired vegetation in cereals and for destroying broad-leaved weeds in soybeans. It is noteworthy that the amount used is high, namely about 11 kg/ha. It is true that a broad range of monocotyledonous and dicotyledonous crop plants are mentioned as indicators of the phytotoxicity of the compounds, but typical examples of broad-leaved weeds commonly encountered on arable land are not given.

We have found that substituted N-benzoylanthranilic acid derivatives of the formula I

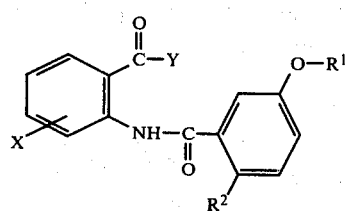

and their anhydro compounds, of the formula II

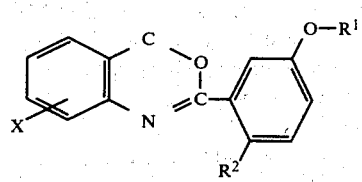

where $R^1$ is a substituted phenyl of the formula

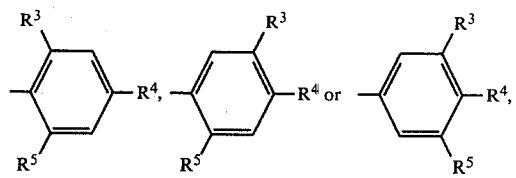

where $R^3$, $R^4$ and $R^5$ are each, independently of one another, hydrogen, halogen, nitro, cyano or carboxyl, or alkyl, haloalkyl, alkoxy, haloalkoxy, alkylmercapto, haloalkylmercapto, alkylsulfinyl or alkylsulfonyl each of 1 to 4 carbon atoms, or $R^1$ is heteroaryl of the formula

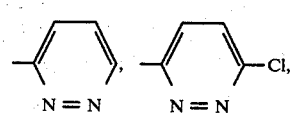

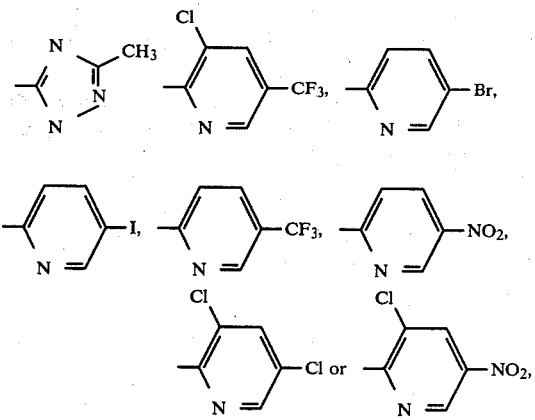

$R^2$ is hydrogen, nitro, cyano or halogen,

X is hydrogen, halogen, nitro or cyano, or is alkyl, haloalkyl, alkoxy, haloalkoxy, haloalkylmercapto or alkylmercapto, each of 1 to 4 carbon atoms, and Y is —$OR^6$ or

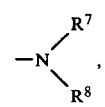

where $R^6$ is hydrogen or alkyl, alkenyl or alkynyl each of up to 4 carbon atoms, or one equivalent of an alkaline earth metal cation or of an alkali metal cation or of an ammonium ion which is unsubstituted or substituted by alkyls of 1 to 4 carbon atoms, and $R^7$ and $R^8$ independently of one another are hydrogen or alkyl of 1 to 4 carbon atoms, display a selective herbicidal action at relatively low doses.

$R^1$ in the formulae I and II may be substituted phenyl of the formula

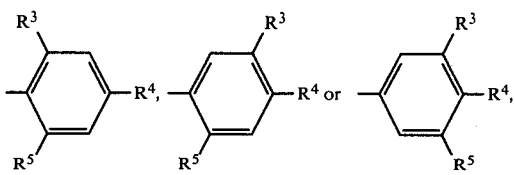

where $R^3$, $R^4$ and $R^5$ are each, for example, independently of one another hydrogen, fluorine, chlorine, bromine, iodine, nitro, cyano, carboxyl, methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl or ethylsulfonyl; $R^1$ may also be heteroaryl, eg.

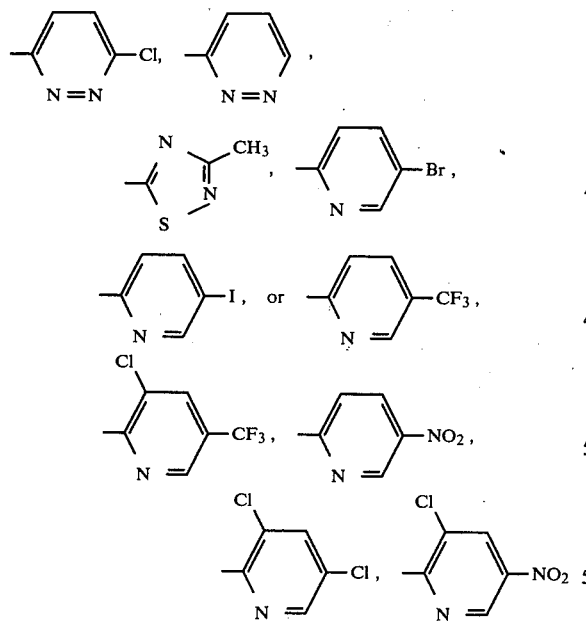

$R^2$ may be hydrogen, nitro, cyano, fluorine, chlorine, iodine or bromine.

X may be, for example, hydrogen, fluorine, chlorine, bromine, iodine, nitro, cyano, methyl, ethyl, n-propyl, 2-propyl, n-butyl, tert.-butyl, trifluoromethyl, trichloromethyl, methoxy, ethoxy, trifluoromethoxy, trichloromethoxy, methylmercapto, ethylmercapto, trichloromethylmercapto or trifluoromethylmercapto.

Y is —O—$R^6$ or

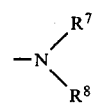

where $R^6$ is, for example, hydrogen, methyl, ethyl, n-propyl, i-propyl, n-butyl, sec.-butyl, isobutyl, tert.-butyl, vinyl, prop-1-enyl, allyl, crotyl, methallyl, 1-methyl-prop-2-enyl, but-4-enyl, 1,2-dimethyl-prop-2-enyl, 2-methylbut-2-en-1-yl, 3-methyl-but-2-enyl, 1,1-dimethyl-prop-2-enyl, 3-methylbut-4-enyl, hex-5-enyl, ethynyl, prop-1-ynyl, propargyl, but-2-ynyl, 1-methyl-prop-2-ynyl, but-4-ynyl, 1,1-dimethyl-prop-2-ynyl, a lithium, potassium, sodium, ammonium, methylammonium, ethylammonium, dimethylammonium, trimethylammonium, triethylammonium, tetramethylammonium or tetraethylammonium ion or one equivalent of calcium ions or magnesium ions, and $R^7$ and $R^8$ independently of one another are hydrogen, methyl, ethyl, n-propyl, i-propyl, n-butyl, sec.-butyl or isobutyl.

Preferred compounds are those where $R^1$ is phenyl which is substituted by halogen and/or haloalkyl, especially by chlorine or trifluoromethyl, $R^2$ is hydrogen or nitro, X is hydrogen, halogen or alkyl or alkoxy each of 1 to 4 carbon atoms, especially hydrogen, chlorine, methyl or methoxy and Y, in the case of a compound of the formula I, is —$OR^6$, where $R^6$ is hydrogen, alkyl of 1 to 4 carbon atoms, especially methyl, or an alkali metal cation.

The N-benzoylanthranilic acid derivatives of the formula I are obtained by reacting an anthranilic acid derivative of the formula III

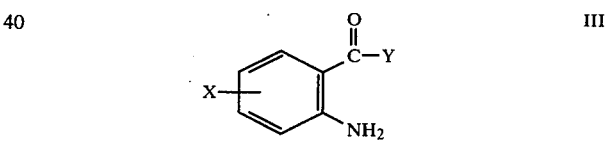

where X and Y have the above meanings, with about the stoichiometric amount of a substituted benzoyl halide of the formula IV

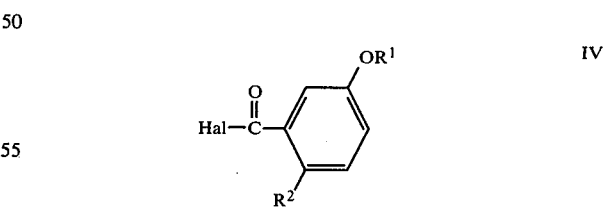

where $R^1$ and $R^2$ have the above meanings and Hal is halogen, especially fluorine, chlorine or bromine, in an aqueous alkaline medium or, where appropriate, in an inert organic solvent in the presence of an acid-binding agent, at from $-30°$ to $+150°$ C.

If anthranilic acid and 3-(3'-chloro-4'-trifluoromethyl-phenoxy)-benzoyl chloride are used as starting materials, the course of the reaction can be represented by the following equation:

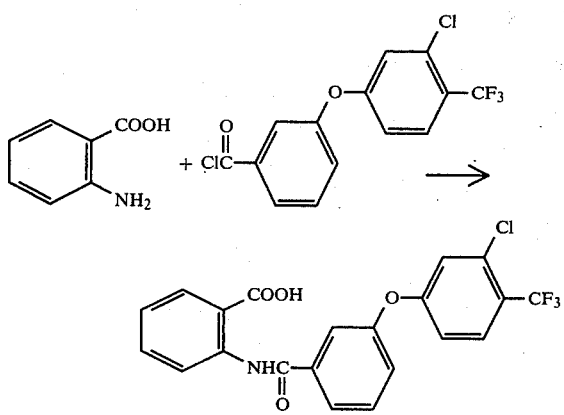

Advantageously, the anthranilic acid derivative of the formula III is reacted with about an equimolar amount of a benzoyl halide of the formula IV and at least an equimolar amount (based on both starting materials) of alkali metal hydroxide, in an aqueous medium (J. Org. Chem. 9 (1944), 396–400). The reaction can, where required, also be carried out in an inert organic solvent in the presence of an acid-binding agent. For both methods, the reaction temperature may be from −30° to +150° C., preferably from +20° to +80° C.

The reaction may be carried out batchwise or continuously.

Suitable inert organic solvents are hydrocarbons, eg. naphtha, gasoline, toluene, pentane, hexane, cyclohexane and petroleum ether; aliphatic and aromatic halohydrocarbons, eg. methylene chloride, chloroform, carbon tetrachloride, 1,1- and 1,2-dichloroethane, 1,1,1- and 1,1,2-trichloroethane, chlorobenzene, o-, m- or p-dichlorobenzene and o-, m- or p-chlorotoluene; aliphatic and aromatic nitrohydrocarbons, eg. nitrobenzene, nitroethane and o-, m- and p-nitrotoluene; nitriles, eg. acetonitrile, butyronitrile and isobutyronitrile; ethers, eg. diethyl ether, di-n-propyl ether, tetrahydrofuran and dioxane; esters, eg. ethyl acetoacetate, ethyl acetate or isobutyl acetate, and amides, eg. formamide, methylformamide and dimethylformamide.

Examples of suitable acid-binding agents are alkali metal hydroxides, alkali metal carbonates and tertiary organic bases. Sodium hydroxide, sodium carbonate, sodium bicarbonate, triethylamine, pyridine, trimethylamine α-, β- and γ-picoline, lutidines, N,N-dimethylaniline, N,N-dimethylcyclohexylamine, quinoline, tri-n-propylamine, tri-n-butylamine and acridine are particularly suitable.

The starting materials I and II may be added in optional sequence.

The compounds of the formula I can be isolated from the reaction mixture by first filtering off the precipitate, stirring it with water and filtering off the remaining residue. If the end product is soluble in the solvent, the latter is stripped off under reduced pressure, the residue is taken up in an alkali metal hydroxide solution, and the resulting solution is filtered and then treated with acid. To isolate the end product, the mixture is filtered and the residue is recrystallized or subjected to chromatography.

The anhydro compounds of the formula II can be prepared by reacting an anthranilic acid derivative of the formula V

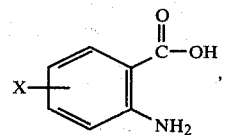

where X has the above meanings, with not less than a one-fold molar excess of a substituted benzoyl halide of the formula IV

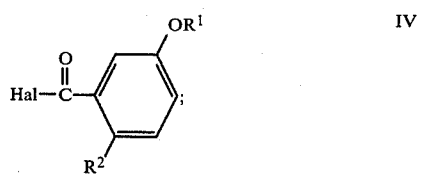

where $R^1$ and $R^2$ have the above meanings, and Hal is halogen, especially fluorine, chlorine or bromine, in the presence of an aromatic tertiary amine, at from 0° to 150° C.

If anthranilic acid and a one-fold molar amount of 3-(3′-chloro-4′-trifluoromethyl-phenoxy)-benzoyl chloride are used, in the presence of pyridine as the tertiary aromatic amine, the course of the reaction can be represented by the following equation:

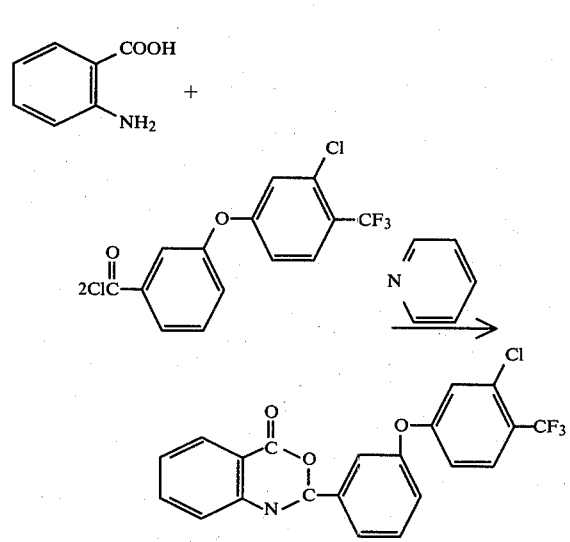

Examples of suitable aromatic tertiary amines are pyridine, quinoline, α-, β- and γ-picoline, acridine and α- and γ-lutidine. From 2 to 10 moles of amine are used per mole of anthranilic acid derivative of the formula V.

To carry out the reaction, the benzoyl halide is advantageously run into the solution of the anthranilic acid derivative in the amine. The reaction can be carried out continuously or batchwise. The reaction temperature used is from 0° to 150° C., preferably from 20° to 80° C. (J. Chem. Soc. (c) (1968), 1593–1597).

The compounds of the formula II may be isolated by stirring the reaction mixture into water. The precipitate formed is filtered off, if necessary washed with alkali to remove traces of acidic impurities, and then purified by recrystallization or chromatography.

Anhydro compounds of the formula II may also be obtained by cyclizing an N-benzoyl-anthranilic acid derivative of the formula I in the presence of a dehydrating agent at from 0° to 150° C.

If N-3-(3'-chloro-4'-trifluoromethyl-phenoxy)benzoylanthranilic acid is used as the starting material for preparing the anhydro compound by treatment with a dehydrating agent, the course of the reaction may be represented by the following equation:

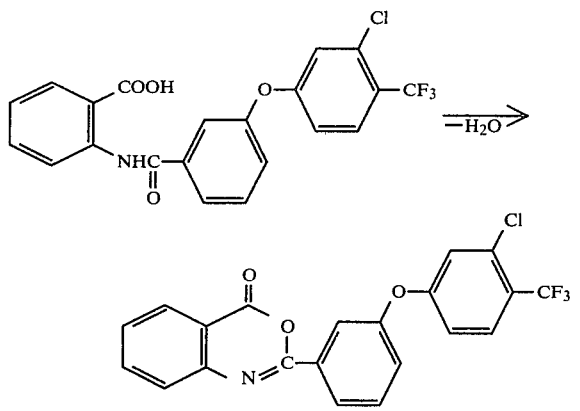

The preferred dehydrating agents include carboxylic acid anhydrides, eg. acetic anhydride, propionic anhydride, butyric anhydride, mixed carboxylic acid anhydrides, such as formic-acetic anhydride, formicpropionic anhydride, formic-butyric anhydride, aceticpropionic anhydride, acetic-butyric anhydride and propionic-butyric anhydride, and dicyclohexylcarbodiimide and thionyl chloride. The cyclization is carried out by means of from 1 to 10 moles of dehydrating agent per mole of N-benzoyl-anthranilic acid derivative of the formula I.

The reaction can be carried out at from 0° to 150° C., preferably from 50° to 100° C., for from 30 minutes to 5 hours, continuously or batchwise.

The end products are isolated from the reaction solution by concentrating the reaction mixture to dryness. The residue left can, if necessary, be washed with alkali to remove traces of acidic impurities, and can then be purified by recrystallization or chromatography (J. Org. Chem. 14 (1949), 967–981).

The benzoyl halides of the formula IV, required as starting materials, may be prepared by conventional methods from the corresponding benzoic acids (Houben-Weyl, Methoden der organ. Chem., Volume 8, page 463 et seq., Georg Thieme-Verlag, Stuttgart, 1952). The phenoxysubstituted and heteroaryloxy-substituted benzoic acids may be obtained by a Williamson ether synthesis from the phenolate of the particular 3-hydroxybenzoic acid and the corresponding halobenzene.

The Examples which follow illustrate the preparation of the novel compounds of the formulae I and II. Parts by weight bear the same relation to parts by volume as that of the kilogram to the liter.

EXAMPLE 1

A solution of 190 parts by volume of 3-(2'-chloro-4'-trifluoromethyl-phenoxy)-6-nitrobenzoyl chloride in 120 parts by volume of absolute diethyl ether, and, separately, 50.5 parts by weight of triethylamine, are simultaneously added dropwise to a solution of 75.58 parts by weight of methyl anthranilate in 500 parts by volume of absolute diethyl ether at room temperature. The reaction mixture is then heated to the reflux temperature, stirred for a further hour under reflux, cooled and filtered. The filter residue is stirred into 2,000 parts by weight of water and then filtered off. 240 parts by weight (97% of theory) of methyl N-3'-(2''-chloro-4''trifluoromethyl-phenoxy)-6'-nitrobenzoyl-anthranilate, of melting point 123°–126° C., are obtained.

Analysis: Calculated: C 52.5; H 2.5; N 5.8; Cl 7.4; F 11.85. Found: C 52.6; H 2.8; N 5.8; Cl 7.4; F 11.4.

EXAMPLE 2

247 parts by weight of methyl N-3'-(2''-chloro-4''-trifluoromethyl-phenoxy)-6'-nitrobenzoylanthranilate are refluxed for one hour with a solution of 33.7 parts by weight of potassium hydroxide in 200 parts by weight of water and 200 parts by volume of ethanol. The mixture is then cooled and the clear reaction solution is acidified with 3 N hydrochloric acid. Hereupon an oil separates out, and this is taken up in diethyl ether. On adding petroleum ether, a crystalline product is obtained; this is filtered off, giving 200 parts by weight (83% of theory) of N-3'-(2''-chloro-4''-trifluoromethyl-phenoxy)-6'-nitrobenzoylanthranilic acid, of melting point 187°–192° C.

Analysis: Calculated: C 52.5; H 2.5; N 5.8; Cl 7.4; F 11.85. Found: C 52.6; H 2.8; N 5.8; Cl 7.4; F 11.4.

EXAMPLE 3

18.1 parts by weight of 3-(2'-chloro-4'-trifluoromethyl-phenoxy)-6-nitrobenzoyl chloride in 40 parts by volume of absolute tetrahydrofuran and, separately, 5.1 parts by weight of triethylamine are simultaneously added dropwise to a solution of 6.9 parts by weight of anthranilic acid in 100 parts by volume of absolute tetrahydrofuran at room temperature. The reaction mixture is then heated to the reflux temperature and stirred for a further hour under reflux. When the mixture has cooled, it is filtered and the filtrate is concentrated. The oily residue is taken up in 40 parts of volume of diethyl ether and the solution is extracted once with dilute hydrochloric acid and then twice with 1 N sodium hydroxide solution. The combined alkaline phases are then acidified with 2 N hydrochloric acid and the product is filtered off. 10 parts by weight (42% of theory) of N-3'-(2''-chloro-4''-trifluoromethylphenoxy)-6'-nitrobenzoylanthranilic acid, of melting point 182°–185° C., are obtained.

Analysis: Calculated: C 52.5; H 2.5; N 5.8; Cl 7.8; F 11.85. Found: C 52.2; H 2.2; N 5.9; Cl 7.2; F 10.9.

EXAMPLE 4

24 parts by weight of N-3'-(2''-chloro-4''-trifluoromethyl-phenoxy)-6-nitrobenzoylanthranilic acid are introduced into a solution of 2 parts by weight of sodium hydroxide in 100 parts by volume of absolute methanol and the mixture is stirred for one hour at room temperature. The solution is then concentrated, leaving a residue of 25 parts by weight (100% of theory) of sodium N-3'-(2''-chloro-4''-trifluoromethyl-phenoxy)-6'-nitrobenzoylanthranilate.

Analysis: Calculated: C 50.2; H 2.2; N 5.6; Cl 7.1; Na 4.6. Found: C 49.9; H 2.6; N 5.6; Cl 7.0; Na 4.0.

EXAMPLE 5

24 parts of N-3-(2'-chloro-4'-trifluoromethyl)-phenoxy-6-nitrobenzoylanthranilic acid are refluxed with 200 parts of acetic anhydride for four hours. The mixture is filtered and the filtrate is concentrated to dryness under reduced pressure. Recrystallization of the residue from ethanol gives 18 parts (78% of theory) of 2-[3'-(2''-chloro-4''-trifluoromethyl-phenoxy)-6'-nitrophenyl]-4H-1,3-benzoxazin-4-one, of melting point 131°–135° C.

Analysis: Calculated: C 54.51; H 2.18; N 6.05; Cl 7.66; F 12.32. Found: C 54.2; H 2.3; N 5.9; Cl 7.2; F 12.0.

Similar methods may be used to synthesize, for example, the following compounds of the formulae I and II.

(a) Compounds of the formula I

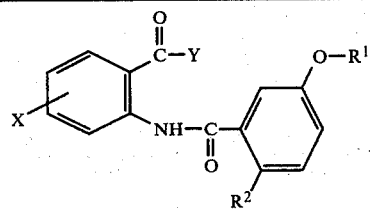

| No. | R¹ | R² | X | Y | M.p. [°C.] |
|---|---|---|---|---|---|
| 6 | phenyl | H | H | OH | |
| 7 | phenyl | NO₂ | H | OH | |
| 8 | 4-Cl-phenyl | H | H | OH | |
| 9 | 4-Cl-phenyl | NO₂ | H | OH | |
| 10 | 2,4-diCl-phenyl | H | H | OH | |
| 11 | 2,4-diCl-phenyl | NO₂ | H | OH | 125–130 |
| 12 | 2-Cl-4-F-phenyl | H | H | OH | |
| 13 | 2-Cl-4-F-phenyl | NO₂ | H | OH | |
| 14 | 2,4-diF-phenyl | H | H | OH | |
| 15 | 2,4-diF-phenyl | NO₂ | H | OH | |
| 16 | 2,3,4-triCl-phenyl | H | H | OH | |
| 17 | 2,3,4-triCl-phenyl | NO₂ | H | OH | |
| 18 | 2,3,4-triF-phenyl | H | H | OH | |
| 19 | 2,3,4-triF-phenyl | NO₂ | H | OH | |

-continued

I

No. | R¹ | R² | X | Y | M.p. [°C.]
--- | --- | --- | --- | --- | ---
20 | 3-Cl-4-CF₃-phenyl | H | H | OH | 178–183
21 | 3-Cl-4-CF₃-phenyl | H | H | OCH₃ | 88–92
22 | 3,5-diCl-4-CF₃-phenyl | H | H | OH | 
23 | 3,5-diCl-4-CF₃-phenyl | NO₂ | H | OH | 
24 | 4-NO₂-phenyl | H | H | OCH₃ | 125–127
25 | 4-NO₂-phenyl | H | H | OH | 204–206
26 | 3-Cl-4-NO₂-phenyl | H | H | OH | 197–201
27 | 3-Cl-4-NO₂-phenyl | H | H | OCH₃ | 138–141
28 | 3-Cl-4-NO₂-phenyl | NO₂ | H | N(C₂H₅)₂ | 
29 | 3-Cl-4-CN-phenyl | H | H | OH | 
30 | 3-Cl-4-CN-phenyl | NO₂ | H | OH | 
31 | 3-Cl-4-SO₂CH₃-phenyl | H | H | OH | 
32 | 3-Cl-4-SCH₃-phenyl | H | H | OH | 
33 | 3-NO₂-4-CF₃-phenyl | H | H | OH | 201–203

-continued
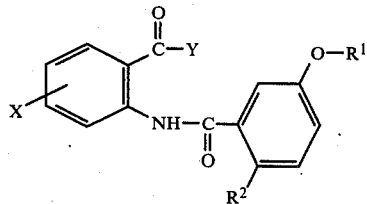
| No. | R¹ | R² | X | Y | M.p. [°C.] |
|---|---|---|---|---|---|
| 34 | 4-CF₃, 3-O₂N phenyl | H | H | OCH₃ | 129–131 |
| 35 | 4-CF₃, 2-Cl phenyl | H | 3-OCH₃ | OH | |
| 36 | 4-CF₃, 2-Cl phenyl | NO₂ | 3-OCH₃ | OH | 185–192 |
| 37 | 4-CF₃, 2-Cl phenyl | NO₂ | 6-Cl | OH | 130–135 |
| 38 | 4-CF₃, 2-Cl phenyl | NO₂ | 6-F | OH | 162–164 |
| 39 | 4-CF₃, 2-Cl phenyl | H | 3-CH₃ | OH | 156–159 |
| 40 | 4-CF₃, 2-Cl phenyl | H | 3-CH₃ | OCH₃ | 83–87 |
| 41 | 4-CF₃, 2-Cl phenyl | H | 3-CH₃ | ONa | [ν$_{C=O}$ = 1580 cm⁻¹] |
| 42 | 4-CF₃, 2-Cl phenyl | NO₂ | 3-CH₃ | OH | 216–219 |
| 43 | 4-CF₃, 2-Cl phenyl | H | 3-Cl | OH | 120–126 |
| 44 | 4-CF₃, 2-Cl phenyl | NO₂ | 3-Cl | OH | 209–211 |
| 45 | 4-CF₃, 2-Cl phenyl | NO₂ | 3-Cl | OCH₃ | 140–143 |
| 46 | 4-CF₃, 2-Cl phenyl | H | 3-F | OH | |
| 47 | 4-CF₃, 2-Cl phenyl | NO₂ | 3-F | OH | |

-continued

| No. | R¹ | R² | X | Y | M.p. [°C.] |
|---|---|---|---|---|---|
| 48 | (phenyl with CF₃, NO₂) | NO₂ | H | OCH₃ | 169–172 |
| 49 | (phenyl with CF₃, NO₂) | NO₂ | H | OH | 181–185 |
| 50 | (phenyl with CF₃, Cl) | H | 4-Cl | OH | |
| 51 | (phenyl with CF₃, Cl) | NO₂ | 4-Cl | OCH₃ | 186–189 |
| 52 | (phenyl with CF₃, Cl) | NO₂ | 4-Cl | OH | 230–232 |
| 53 | (phenyl with CF₃, Cl) | NO₂ | 4-Cl | ONa | [ν$_{C=O}$ = 1670 cm$^{-1}$] |
| 54 | (phenyl with OCH₃, Cl) | NO₂ | H | OH | |
| 55 | (phenyl with OCF₃, Cl) | NO₂ | H | OH | |
| 56 | (phenyl with CF₃, Cl) | CN | H | OH | |
| 57 | (phenyl with CF₃, Cl) | NO₂ | H | N(CH₃)₂ | 174–177 |
| 58 | (phenyl with CF₃, Cl) | NO₂ | H | N(CH₃)₂ | 155–158 |
| 59 | (phenyl with CF₃, Cl) | NO₂ | H | NH–cyclopropyl | 170–175 |
| 60 | (phenyl with CF₃, Cl) | H | H | OCH₃ | 100–104 |
| 61 | (phenyl with CF₃, Cl) | H | H | OH | 153–156 |

-continued
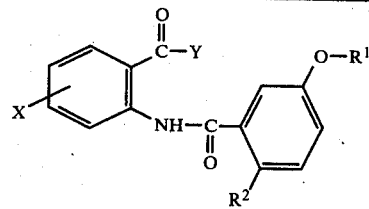
| No. | R¹ | R² | X | Y | M.p. [°C.] |
|---|---|---|---|---|---|
| 62 | (3-Cl, 4-CF₃-phenyl) | H | H | ONa | [ν$_{C=O}$ = 1680 cm⁻¹] |
| 63 | (3-Cl, 4-CF₃-phenyl) | NO₂ | H | OH | |
| 64 | (3-Cl, 4-CF₃-phenyl) | NO₂ | H | OCH₃ | 85–92 |
| 65 | (3-Cl, 4-CF₃-phenyl) | NO₂ | H | ONa | [ν$_{C=O}$ = 1660 cm⁻¹] |
| 66 | (3-Cl, 4-CF₃-phenyl) | NO₂ | 5-Cl | OH | 223–227 |
| 67 | (4-Cl, 3-CF₃-phenyl) | H | H | OH | 200–204 |
| 68 | (4-Cl, 3-CF₃-phenyl) | H | H | OCH₃ | 98–102 |
| 69 | (4-Cl, 3-CF₃-phenyl) | NO₂ | H | OH | |
| 70 | (4-NO₂, 3-CF₃-phenyl) | H | H | OH | 184–187 |
| 71 | (4-NO₂, 3-CF₃-phenyl) | H | H | OCH₃ | 142–146 |
| 72 | (4-NO₂, 3-CF₃-phenyl) | H | H | ONa | [ν$_{C=O}$ = 1650 cm⁻¹] |
| 73 | (3,5-diCl, 4-CF₃-phenyl) | H | H | OH | |
| 74 | (3-F, 4-CF₃-phenyl) | H | H | OH | |
| 75 | (3-F, 4-CF₃-phenyl) | NO₂ | H | OH | |

-continued
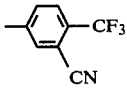   I
| No. | R¹ | R² | X | Y | M.p. [°C.] |
|---|---|---|---|---|---|
| 76 |  | NO₂ | H | OH | |
| 77 |  | NO₂ | H | OH | |
| 78 |  | H | H | OH | |
| 79 |  | NO₂ | H | OH | |
| 80 |  | NO₂ | H | OH | |
| 81 |  | NO₂ | H | OH | |
| 82 |  | NO₂ | H | OH | |
| 83 | 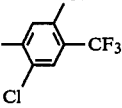 | NO₂ | H | OH | |
| 84 |  | NO₂ | H | OH | |
| 85 |  | NO₂ | H | OH | |
| 86 |  | NO₂ | H | OH | |
| 87 | 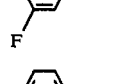 | NO₂ | H | OH | |
| 88 |  | NO₂ | H | OH | |

-continued
$$\text{I}$$
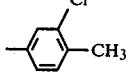
| $R^1$ | $R^2$ | X | Y | M.p. [°C.] |
|---|---|---|---|---|
|  | NO₂ | H | OH | |
| 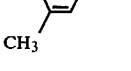 | NO₂ | H | OH | |
|  | H | H | OH | |
|  | H | H | OH | 188–191 |
| 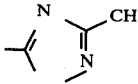 | H | H | OH | |
| 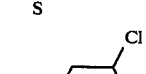 | H | H | OH | |
| 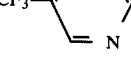 | H | H | OH | 135–138 |
| 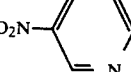 | H | H | OCH₃ | 154–156 |
| 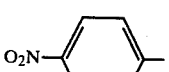 | H | H | OH | |
| 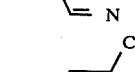 | H | H | OH | |
| 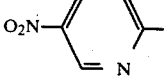 | H | H | OCH₃ | 150–152 |
|  | H | H | OH | 204–207 |

-continued

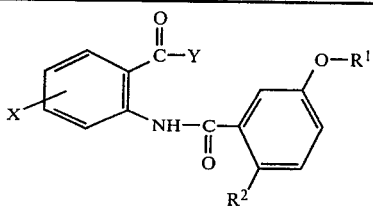

I

| No. | R¹ | R² | X | Y | M.p. [°C.] |
|---|---|---|---|---|---|
| 101 | 5-Bromo-pyridin-2-yl | H | H | ONa | |
| 102 | 4-CF₃-2-Cl-phenyl | NO₂ | 3-CH₃ | OCH₃ | 170–173 |
| 103 | 4-CF₃-2-Cl-phenyl | NO₂ | 3-OCH₃ | OCH₃ | 150–154 |
| 104 | 4-O₂N-phenyl | H | H | ONa | [$\nu_{C=O}$ = 1640 cm⁻¹] |
| 105 | 4-CF₃-2-Cl-phenyl | NO₂ | 5-Cl | OH | 223–227 |
| 106 | 3-Cl-6-methyl-pyridazin-yl | H | H | OCH₃ | 166–168 |
| 107 | 3-CF₃-Cl-phenyl | H | H | ONa | [$\nu_{C=O}$ = 1580 cm⁻¹] |
| 108 | 4-CF₃-2-Cl-phenyl | H | 6-Cl | OCH₃ | $n_D^{25}$ = 1.5858 |
| 109 | 4-CF₃-2-Cl-phenyl | H | 6-Cl | OH | 181–185 |
| 110 | 3-CF₃-Cl-phenyl | H | 6-Cl | ONa | [$\nu_{C=O}$ = 1600 cm⁻¹] |

(b) Compounds of the formula II

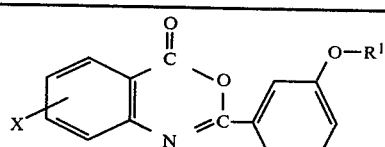

II

| No. | R¹ | R² | X | M.p. [°C.] |
|---|---|---|---|---|
| 111 | 4-Cl-phenyl | H | H | |
| 112 | 4-Cl-phenyl | NO₂ | H | |

-continued

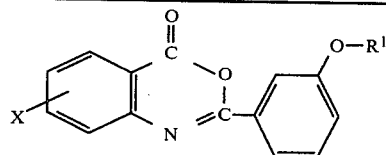

II

| No. | R¹ | R² | X | M.p. [°C.] |
|---|---|---|---|---|
| 113 | 2,4-diCl-phenyl | H | H | |
| 114 | 2,4-diCl-phenyl | NO₂ | H | 165–170 |

-continued

| No. | R¹ | R² | X | M.p. [°C.] |
|---|---|---|---|---|
| 115 | 2-Cl,4-F-phenyl | H | H | |
| 116 | 2-Cl,4-F-phenyl | NO₂ | H | |
| 117 | 2,4-F-phenyl | NO₂ | H | |
| 118 | 3,4-Cl-phenyl | H | H | |
| 119 | 3,4-Cl-phenyl | NO₂ | H | |
| 120 | 3-Cl,4-CF₃-phenyl | H | H | 141–143 |
| 121 | 3,5-Cl,4-CF₃-phenyl | H | H | |
| 122 | 3,5-Cl,4-CF₃-phenyl | NO₂ | H | |
| 123 | 4-NO₂-phenyl | H | H | 193–195 |
| 124 | 3-Cl,4-NO₂-phenyl | H | H | 175–176 |
| 125 | 3-Cl,4-CN-phenyl | NO₂ | H | |
| 126 | 2-NO₂,4-CF₃-phenyl | H | H | 145–147 |
| 127 | 3-Cl,4-CF₃-phenyl | NO₂ | 8-OCH₃ | 175–178 |
| 128 | 3-Cl,4-CF₃-phenyl | NO₂ | 8-CH₃ | 129–134 |
| 129 | 3-Cl,4-CF₃-phenyl | H | 8-CH₃ | 83–87 |
| 130 | 3-Cl,4-CF₃-phenyl | NO₂ | 5-Cl | 161–164 |
| 131 | 3-Cl,4-CF₃-phenyl | NO₂ | 5-F | 109–113 |
| 132 | 3-Cl,4-CF₃-phenyl | NO₂ | 7-Cl | 138–141 |
| 133 | 3-Cl,4-CF₃-phenyl | H | H | 120–122 |
| 134 | 3-Cl,4-CF₃-phenyl | NO₂ | H | |
| 135 | 4-Cl,3-CF₃-phenyl | H | H | 167–169 |
| 136 | 4-Cl,3-CF₃-phenyl | NO₂ | H | |
| 137 | 3-NO₂,4-CF₃-phenyl | H | H | 140–144 |
| 138 | 4-F,3-CF₃-phenyl | H | H | |
| 139 | 3-Cl,4-OCF₃-phenyl | H | H | |
| 140 | 3-Cl,4-OCF₃-phenyl | NO₂ | H | |
| 141 | 3-CN,4-CF₃-phenyl | NO₂ | H | |
| 142 | 3-CN,4-CF₃ (variant) | NO₂ | H | |
| 143 | 3,4-Cl-phenyl | NO₂ | H | |

-continued $$\text{II}$$

Structure II: benzene ring with X substituent, C(=O)-O-... group, N=C connecting to another benzene ring with O-R¹ and R² substituents.

| No. | R¹ | R² | X | M.p. [°C.] |
|---|---|---|---|---|
| 144 | 2-F, 4-CN phenyl (-CH2-C6H3(F)(CN)) | NO2 | H | |
| 145 | 3-Cl, 4-CH3 phenyl | NO2 | H | |
| 146 | 3-CH3, 4-Cl phenyl | NO2 | H | |
| 147 | 2-F, 3-F phenyl | NO2 | H | |
| 148 | pyridazinyl (N=N) | H | H | |
| 149 | 6-Cl-pyridazinyl | H | H | 167–170 |
| 150 | 3-CF3, 4-Cl-pyridyl | H | H | |
| 151 | 4-CH3-thiazolyl | H | H | |
| 152 | 2-Cl, 4-Cl-pyridyl | H | H | |
| 153 | 4-O2N-pyridyl | H | H | |
| 154 | 2-O2N, 4-Cl-pyridyl | H | H | |
| 155 | 4-Br-pyridyl | H | H | 152–154 |
| 156 | 3-F3C, 4-Cl phenyl | H | 8-Cl | 120–128 |
| 157 | 3-F3C, 4-Cl phenyl | H | 5-Cl | 150–153 |

In view of the good tolerance and the many application methods possible, the herbicides according to the invention, or mixtures containing them, may be used in a large number of other crops for eliminating unwanted growth. The application rates depend on the composition and growth stages of the weed flora, and vary from 0.1 to 15, and preferably from 0.2 to 3.0, kg per hectare.

The following crop plants are given by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rape |
| *Brassica napus* var. napobrassica | |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium Gossypium arborium* *Gossypium herbaceum* *Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. tuberosum | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | |
| *Ricinus communis* | |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. vulgare) | grain sorghum |
| *Sorghum dochna* | |

| Botanical name | Common name |
| --- | --- |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated caster oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

Examples of formulations are given below.

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of caster oil. By pouring the solution into 100,000 parts by weight of water and uniformly distributing it therein, an aqueous dispersion is obtained containing 0.02% by weight of the active ingredient.

III. 20 parts by weight of compound no. 37 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of caster oil. By pouring the solution into 100,000 parts by weight of water and finely distributing it therein, an aqueous dispersion is obtained containing 0.02% by weight of the active ingredient.

IV. 20 parts by weight of the compound of Example 5 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 4 is well mixed with 3 parts by weight of the sodium salt of diisobutylnaphthalene-α-sulfonic acids, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 20 is intimately mixed with 97 parts by weight of particulate kaolin. A dust is obtained containing 3% by weight of the active ingredient.

VII. 30 parts by weight of compound no. 96 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 11 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The N-benzoylanthranilic acid derivatives of the formula I and their anhydro compounds of the formula II may be mixed with each other or mixed and applied together with numerous representatives of other herbicidal or growth-regulating active ingredient groups. Examples of suitable mixture components are diazines, benzothiadiazinones, 2,6-dinitroanilines, N-phenylcarbamates, biscarbamates, thiolcarbamates, halocarboxylic acids, triazines, amides, ureas, diphenyl ethers, triazinones, uracils, benzofuran derivatives, etc. Such combinations broaden the spectrum of action and synergistic effects are sometimes achieved. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone 5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone 3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate 2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl, N,N-di-n-propylthiolcarbamate
n-propyl N,N-di-n-propylthiocarbamate
2,3-dichloroallyl N,N-diisopropylthiolcarbamate 2,3,3-trichloroallyl N,N-diisopropylthiolcarbamate
3-methyl-5-isoxazolylmethyl N,N-diisopropylthiolcarbamate
3-ethyl-5-isoxazolylmethyl, N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1.]-heptylthiolcarbamate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate n-propyl N-ethyl-N-n-butylthiolcarbamate
2-chloroallyl, N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid—(salts, esters, amides)
2,3,6-trichlorobenzoic acid—(salts, esters, amides)
2,3,5,6-tetrachlorobenzoic acid—(salts, esters, amides)
2-methoxy-3,6-dichlorobenzoic acid—(salts, esters, amides)
2-methoxy-3,5,6-trichlorobenzoic acid—(salts, esters, amides)
3-amino-2,5,6-trichlorobenzoic acid—(salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine 2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione 3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil 2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide 2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide 2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide 2-(2-methyl-4-chlorophenoxy)-N-methoxyacetamide
2-(-naphthoxy)-N,N-diethylpropionamide
2,2-diphenyl-N,N-dimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
N-2,4-dimethyl-5-(trifluoromethyl)-sulfonylaminophenylacetamide
N-4-methyl-5-(trifluoromethyl)-sulfonylaminophenylacetamide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile 3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol—(salts, esters)
2-sec.butyl-4,6-dinitrophenol—(salts, esters)
2-sec.butyl-4,6-dinitrophenol acetate
2-tert.butyl-4,6-dinitrophenol acetate
2-tert.butyl-4,6-dinitrophenol—(salts)
2-tert.butyl-5-methyl-4,6-dinitrophenol—(salts)
2-tert.butyl-5-methyl-4,6-dinitrophenol acetate 2-sec.amyl-4,6-dinitrophenol—(salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide 3-[1-(N-ethoxyamino)-propylidene]-6-ethyl-3,4-dihydro-2H-pyran-2,4-dione 3-[1-(N-allyloxyamino)-propylidene]-6-ethyl-3,4-dihydro-2H-pyran-2,4-dione 2-[1-(N-allyloxyamino)-propylidene]-5,5-dimethylcyclohexane-1,3-dione (salts)

2-[1-(N-allyloxyamino-butylidene]-5,5-dimethylcyclohexane-1,3-dione (salts)

2-[1-(N-allyloxyamino-butylidene]-5,5-dimethyl-4-methoxycarbonylcyclohexane-1,3-dione (salts)

2-chlorophenoxyacetic acid—(salts, esters, amides)

4-chlorophenoxyacetic acid—(salts, esters, amides)

2,4-dichlorophenoxyacetic acid—(salts, esters, amides)

2,4,5-trichlorophenoxyacetic acid—(salts, esters, amides)

2-methyl-4-chlorophenoxyacetic acid—(salts, esters, amides)

3,5,6-trichloro-2-pyridinyl-oxyacetic acid—(salts, esters, amides)

methyl α-naphthoxyacetate 2-(2-methylphenoxy)-propionic acid—(salts, esters, amides)

2-(4-chlorophenoxy)-propionic acid—(salts, esters, amides)

2-(2,4-dichlorophenoxy)-propionic acid—(salts, esters, amides)

2-(2,4,5-trichlorophenoxy)-propionic acid—(salts, esters, amides)

2-(2-methyl-4-chlorophenoxy)-propionic acid—(salts, esters, amides)

4-(2,4-dichlorophenoxy)-butyric acid—(salts, esters, amides)

4-(2-methyl-4-chlorophenoxy)-butyric acid—(salts, esters, amides)

cyclohexyl-3-(2,4-dichlorophenoxy)-acrylate 9-hydroxyfluorenecarboxylic acid-(9)—(salts, esters)

2,3,6-trichlorophenylacetic acid—(salts, esters)

4-chloro-2-oxobenzothiazolin-3-yl-acetic acid—(salts, esters)

gibelleric acid (salts)

disodium methylarsonate monosodium salt of methylarsonic acid

N-phosphonomethyl-glycine (salts)

N,N-bis-(phosphonomethyl)-glycine (salts)

2-chloroethyl 2-chloroethanephosphonate ammonium-ethyl-carbamoyl-phosphonate di-n-butyl-1-n-butylamino-cyclohexyl-phosphonate trithiobutylphosphite O,O-diisopropyl-5-(2-benzosulfonylaminoethyl)-phosphorodithionate 2,3-dihydro-5,6-dimethyl-1,4-dithiin-1,1,4,4-tetraoxide 5-tert.butyl-3-(2,4-dichloro-5-isopropoxyphenyl)-1,3,4-oxadiazolone-(2)

4,5-dichloro-2-trifluoromethylbenzimidazole—(salts)

1,2,3,6-tetrahydropyridazine-3,6-dione—(salts)

succinic acid mono-N-dimethylhydrazide—(salts)

(2-chloroethyl)-trimethylammonium chloride (2-methyl-4-phenylsulfonyl)-trifluoromethanesulfone anilide 1,1-dimethyl-4,6-diisopropyl-5-indanyl ethyl ketone 2-[1-(2,5-dimethylphenyl)-ethylsulfonyl]-pyridine-N-oxide sodium chlorate ammonium thiocyanate calcium cyanamide.

It may also be useful to apply the new compounds, either on their own or in combination with other herbicides, in admixture with other crop protection agents, e.g., agents for combating pests or phytopathogenic fungi or bacteria. The compounds may also be mixed with solutions of mineral matters used to remedy nutritional or trace element deficiencies.

To initiate the herbicidal action, wetting agents, spreader-stickers and non-phytotoxic oils and oil concentrates may be added.

The influence of various representatives of the compounds according to the invention on the growth of unwanted and crop plants is demonstrated in the following greenhouse experiments.

The vessels employed were plastic pots having a volume of 300 cm$^3$ which were filled with a sandy loam containing about 1.5% humus. The seeds of the test plants (cf. Table 1) were sown shallow, and separately, according to species. In the case of Cyperus esculentus, pregerminated tubers were used.

For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 10 cm, depending on growth form, before being treated. Some plant species were sown direct into the pots; others were grown first in cultivation dishes and transplanted a few days before the pots were treated. No cover was placed on the vessels.

The pots were set up in the greenhouse—species from warmer areas at from 25° to 40° C., and species from moderate climates at 15° to 30° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plant species used in the experiments are listed in Table 1.

Tables 2 to 10 illustrate the selective herbicidal action of representatives of the compounds according to the invention. This action is directed, depending on the compound, either specifically against individual broadleaved unwanted plants or simultaneously against broadleaved and grassy unwanted plants; the action also covers Cyperaceae. The agents according to the invention may be applied both pre- and postemergence, the latter being preferred. A special application technique is to spray the active ingredients with the aid of spraying equipment in such a way that the leaves of sensitive crop plants are if possible not hit; the active ingredients reach the soil or unwanted plants growing below the crop plants (post-directed, lay-by treatment).

TABLE 1

| List of plant names | |
|---|---|
| Botanical name | Common name |
| Abutilon theoprasti | velvet leaf |
| Amaranthus retroflexus | redroot pigweed |
| Arachis hypogaea | peanuts (groundnuts) |

TABLE 1-continued

List of plant names

| Botanical name | Common name |
|---|---|
| *Beta vulgaris* | sugarbeets |
| Bromus spp. | brome |
| *Bidens pilosa* | hairy beggarticks |
| *Centaurea cyanus* | cornflower |
| *Chenopodium album* | lambsquarters (goosefoot) |
| *Chrysanthemum segetum* | corn marigold |
| *Cyperus esculentus* | yellow nutsedge |
| *Cyperus ferax* | |
| *Datura stramonium* | Jimsonweed |
| *Digitaria sanguinalis* | large crabgrass |
| *Euphorbia geniculata* | South American member of the spurge family |
| *Glycine max* | soybeans |
| *Helianthus annuus* | sunflowers |
| Ipomoea spp. | morningglory |
| *Nicandra physaloides* | apple-of-Peru |
| *Oryza sativa* | rice |
| *Pisum sativum* | English peas |
| *Polygonum persicaria* | ladysthumb |
| *Sesbania exaltata* | hemp sesbania (coffeeweed) |
| Setaria spp. | foxtail spp. |
| *Asclepias syriaca* | milkweed |
| *Sinapis alba* | white mustard |
| *Solanum nigrum* | black nightshade |
| *Triticum aestivum* | wheat |
| *Zea mays* | Indian corn |
| *Acanthospermum hispidum* | bristly starbur |
| Asclepias spp. | mildweed |
| *Avena fatua* | wild oats |
| *Centaurea cyanus* | cornflower |
| *Hordeum vulgare* | barley |
| *Lamium amplexicaule* | henbit |
| *Mercurialis annua* | annual mercury |
| Viola spp. | pansy |

TABLE 2

Selective removal of lambsquarters from sugarbeets and other crops on postemergence treatment in the greenhouse with the active ingredient of the formula

[Structure: benzene ring with COOH and NH-C(=O)- linking to another benzene ring with O-linked trifluoromethyl-chlorophenyl group] (No. 20)

| Test plants | Damage [%] at rates of | |
|---|---|---|
| | 1.0 | 0.4 kg/ha |
| *Beta vulgaris* | 0 | 0 |
| *Helianthus annuus* | 0 | 0 |
| *Pisum sativum* | 0 | 0 |
| *Chenopodium album* | 99 | 99 |

TABLE 3

Selective control of redroot pigweed in wheat and sugarbeets on postemergence treatment in the greenhouse with the active ingredient of the formula

[Structure with OCH₃, N, and NO₂ substituents linked via O-C to trifluoromethyl-chlorophenyl group] (No. 127)

The comparative agent is the active ingredient of the formula

[Structure] (U.S. Pat. No. 3,914,121).

| Test plants | Damage [%] at a rate of | |
|---|---|---|
| | 0.5 kg of compound no. 120/ha | 0.5 kg of comparative agent/ha |
| *Beta vulgaris* | 10 | 95 |
| *Triticum aestivum* | 10 | 0 |
| *Amaranthus retroflexus* | 90 | 16 |

TABLE 4

Removal of unwanted grasses and Cyperus in various crops on postemergence treatment in the greenhouse with the active ingredient of the formula

[Structure with C(=O)-ONa and NO₂ substituents] (No. 4)

| Test plants | Damage [%] at a rate of 0.4 kg/ha |
|---|---|
| *Arachis hypogaea* | 0 |
| *Glycine max* | 12 |
| *Oryza sativa* | 10 |
| *Pisum sativum* | 0 |
| *Zea mays* | 10 |
| *Cyperus esculentus* | 80 |
| Setaria spp. | 80 |

TABLE 5

Control of large crabgrass in soybeans and rice on postemergence treatment in the greenhouse with the active ingredient of the formula

[Structure with C(=O)-OCH₃ and NO₂ substituents] (No. 1)

| Test plants | Damage [%] at a rate of 0.5 kg/ha |
|---|---|
| *Glycine max* | 0 |

TABLE 5-continued

Control of large crabgrass in soybeans and rice on postemergence treatment in the greenhouse with the active ingredient of the formula

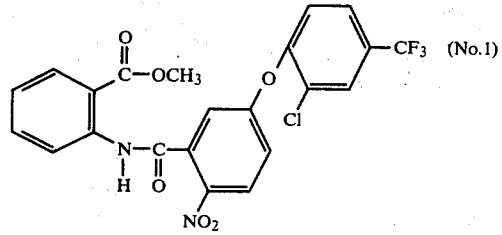
(No. 1)

| Test plants | Damage [%] at a rate of 0.5 kg/ha |
|---|---|
| Oryza sativa | 0 |
| Digitaria sanguinalis | 80 |

TABLE 6

Control of Cyperus spp. in groundnuts and rice on postemergence treatment in the greenhouse with the active ingredient of the formula

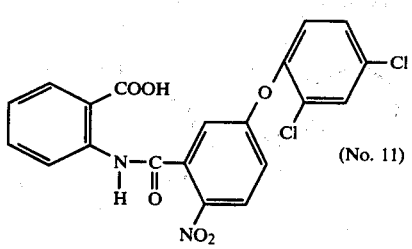
(No. 11)

| Test plants | Damage [%] at rates of | |
|---|---|---|
| | 0.5 | 0.25 kg/ha |
| Arachis hypogaea | 0 | — |
| Oryza sativa | 10 | 0 |
| Cyperus ferax | 100 | 100 |

TABLE 7

Selective control of broadleaved weeds in groundnuts on postemergence treatment in the greenhouse with the active ingredient of the formula

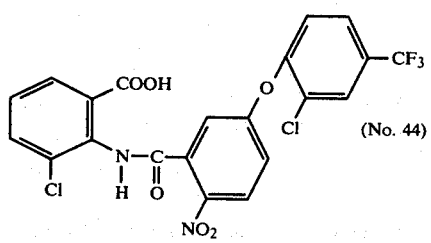
(No. 44)

| Test plants | Damage [%] at a rate of 0.4 kg/ha |
|---|---|
| Arachis hypogaea | 0 |
| Euphorbia geniculata | 85 |
| Solanum nigrum | 80 |

TABLE 8

Control of unwanted plants in various agricultural crops on postemergence treatment in the greenhouse with the active ingredient of the formula

TABLE 8-continued

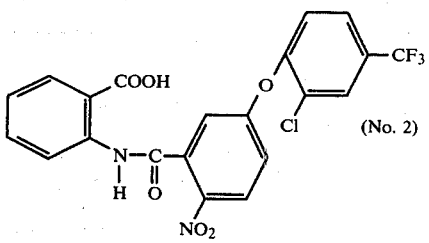
(No. 2)

The comparative agent is the active ingredient of the formula

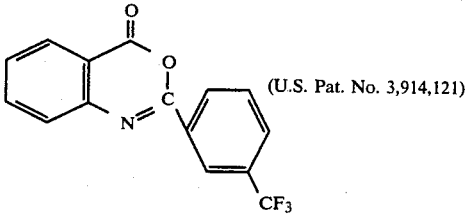
(U.S. Pat. No. 3,914,121)

| Test plants | Damage [%] at a rate of 0.25 kg of compound no. 2/ha | 0.25 kg of comparative compound/ha |
|---|---|---|
| Arachis hypogaea | 10 | 0 |
| Glycine max | 10 | 22 |
| Oryza sativa | 2 | 0 |
| Pisum sativum | 10 | 2 |
| Abutilon theophrasti | 100 | 10 |
| Bromus spp. | 80 | 0 |
| Crysanthemum segetum | 100 | 82 |
| Cyperus ferax | 99 | 30 |
| Digitaria sanguinalis | 90 | 0 |
| Polygonum persicaria | 98 | 60 |
| Sesbania exaltata | 92 | 90 |
| Setaria spp. | 90 | 0 |

TABLE 9

Control of unwanted plant growth on postemergence treatment in the greenhouse with the active ingredient of the formula

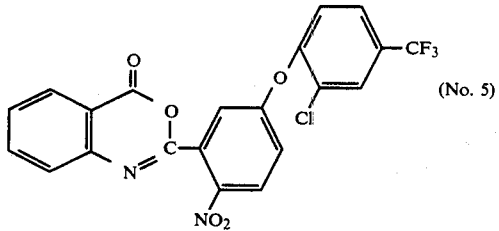
(No. 5)

The comparative agent is the active ingredient of the formula

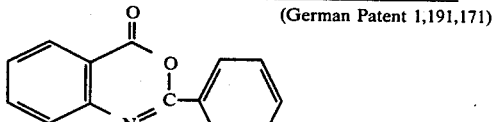
(German Patent 1,191,171)

| Test plants | Damage [%] at a rate of 0.4 kg of compound no. 5/ha | 4.0 kg of comparative agent/ha |
|---|---|---|
| Arachis hypogaea | 5 | 0 |
| Abutilon theophrasti | 98 | 10 |
| Asclepias syriaca | 90 | 0 |
| Bidens pilosa | 95 | 20 |
| Datura stramonium | 85 | 10 |
| Digitaria sanguinalis | 90 | — |
| Euphorbia geniculata | 98 | 20 |
| Nicandra physaloides | 100 | 98 |
| Setaria spp. | 80 | 0 |
| Sinapis alba | 95 | 95 |

TABLE 9-continued

| | | |
|---|---|---|
| Solanum nigrum | 100 | 65 |

TABLE 10

Herbicidal action on pre- and postemergence treatment in the greenhouse

| | | Test plants and damage (%) | | |
|---|---|---|---|---|
| Active | | Preemergence | Postemergence | |
| ingredient no. | Appln. rate [kg/ha] | Sinapis alba | Centaurea cyanus | Ipomoea spp. |
| 42 | 3.0 | 100 | 90 | — |
| 36 | 3.0 | 100 | 90 | 90 |
| 52 | 3.0 | 90 | 90 | — |
| 102 | 3.0 | 100 | 100 | 100 |
| 53 | 3.0 | 90 | 100 | — |
| 132 | 3.0 | — | 90 | 80 |
| 114 | 3.0 | 100 | 100 | 100 |
| 128 | 3.0 | 90 | 100 | 100 |
| 103 | 3.0 | 100 | 100 | 100 |

TABLE 11

Selective control of unwanted broadleaved plants in Gramineae on postemergence treatment in the greenhouse with the active ingredient of the formula

[Structure: benzoxazine with phenoxy-chloro-CF$_3$ phenyl substituent]

(No. 120)

| | Damage [%] at kg/ha | |
|---|---|---|
| Test plants | 1.0 | 2.0 |
| Hordeum vulgare | 0 | 0 |
| Oryza sativa | 10 | 10 |
| Triticum aestivum | 0 | 0 |
| Acanthospermum hispidum | 100 | 100 |
| Asclepias spp. | 98 | 100 |
| Chenopodium album | 100 | 100 |
| Chrysanthemum segetum | 100 | 100 |
| Euphorbia geniculata | 100 | 100 |
| Lamium amplexicaule | 80 | 80 |
| Nicandra physaloides | 100 | 100 |
| Solanum nigrum | 75 | 75 |
| Sinapis alba | 80 | 100 |

0 = no damage
100 = plants completely destroyed

TABLE 12

Selective control of unwanted plants on postemergence treatment in the greenhouse with the active ingredient of the formula

[Structure: 2-acetyl-6-methyl-anilide of 3-(2-chloro-4-CF$_3$-phenoxy)benzoyl]

(No. 40)

| Test plants | Damage [%] at 0.5 kg/ha |
|---|---|
| Triticum aestivum | 5 |
| Amaranthus retroflexus | 100 |
| Avena fatua | 80 |
| Ipomoea spp. | 95 |

0 = no damage
100 = plants completely destroyed

TABLE 13

Control of broadleaved unwanted plants in cereals on postemergence treatment in the greenhouse with the active ingredient of the formula

[Structure: 2-carboxy-6-chloro-anilide of 3-(2-chloro-4-CF$_3$-phenoxy)benzoyl]

(No. 43)

| | Damage [%] at | |
|---|---|---|
| Test plants | 1.0 | 2.0 kg/ha |
| Triticum aestivum | 5 | 5 |
| Centaurea cyanus | 98 | 98 |
| Ipomoea spp. | 100 | 100 |
| Mercurialis annua | 95 | 95 |
| Sinapis alba | 100 | 100 |
| Viola spp. | 80 | 90 |

0 = no damage
100 = plants completely destroyed

We claim:

1. A compound of the formula $$\text{I}$$

[Structure I]

a compound of the formula $$\text{II}$$

[Structure II]

where $R^1$ is a substituted phenyl of the formula

[Three phenyl structures with $R^3$, $R^4$, $R^5$ substituents]

where $R^3$, $R^4$ and $R^5$ are each, independently of one another, hydrogen, halogen, nitro, cyano or carboxyl, or alkyl, haloalkyl, alkoxy, haloalkoxy, alkylmercapto, haloalkylmercapto, alkylsulfinyl or alkylsulfonyl each of 1 to 4 carbon atoms, or $R^1$ is heteroaryl of the formula

[Pyridyl and chloropyridazinyl structures]

-continued

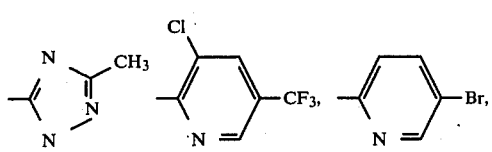

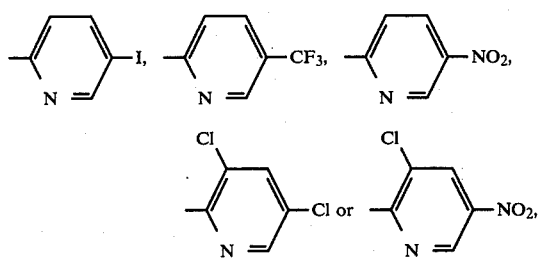

$R^2$ is hydrogen, nitro, cyano or halogen,

X is hydrogen, halogen, nitro or cyano, or is alkyl, haloalkyl, alkoxy, haloalkoxy, haloalkylmercapto or alkylmercapto, each of 1 to 4 carbon atoms, and Y is —$OR^6$ or

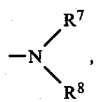

where $R^6$ is hydrogen or alkyl, alkenyl or alkynyl each of up to 4 carbon atoms, or one equivalent of an alkaline earth metal cation or of an alkali metal cation or of an ammonium ion which is unsubstituted or substituted by alkyls of 1 to 4 carbon atoms, and $R^7$ and $R^8$ independently of one another are hydrogen or alkyl of 1 to 4 carbon atoms.

2. A compound of the formula I of claim 1, wherein $R^1$ is a substituted phenyl of the formula

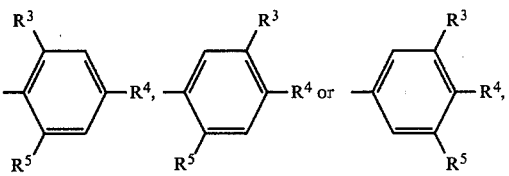

where
$R^3$, $R^4$ and $R^5$ are each, independently of one another, hydrogen, halogen, or haloalkyl of 1 to 4 carbon atoms,
$R^2$ is hydrogen or nitro,
X is hydrogen, halogen, or alkyl or alkoxy, each of 1 to 4 carbon atoms, and
Y is —$OR^6$,
where
$R^6$ is hydrogen, an alkali metal cation or alkyl of up to 4 carbon atoms.

3. A compound of the formula II of claim 1, wherein $R^1$ is a substituted phenyl of the formula

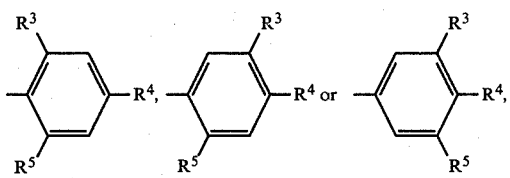

where
$R^3$, $R^4$ and $R^5$ are each, independently of one another, hydrogen, halogen, or haloalkyl of 1 to 4 carbon atoms,
$R^2$ is hydrogen or nitro and,
X is hydrogen, halogen, or alkyl or alkoxy, each of 1 to 4 carbon atoms.

4. The sodium salt of N-3'-(2''-chloro-4''-trifluoromethylphenoxy)-6'-nitrobenzoylanthranilic acid.

5. 2-[3'-(2''-Chloro-4''-trifluoromethylphenoxy)-6'-nitrophenyl]-4H-1,3-benzoxazin-4-one.

6. N-3'-(2''-Chloro-4''-trifluoromethylphenoxy)-benzoylanthranilic acid.

7. A compound of formula II of claim 1, wherein $R^1$ is

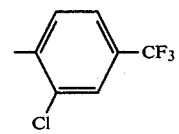

$R^2$ is $NO_2$ and X is 8—$CH_3$.

* * * * *

UNITED STATES PATENT AND TRADEMARK OFFICE
CERTIFICATE OF CORRECTION

PATENT NO. : 4,321,371
DATED : March 23, 1982
INVENTOR(S) : Adolf Parg, Bruno Wuerzer and Gerhard Hamprecht It is certified that error appears in the above-identified patent and that said Letters Patent is hereby corrected as shown below:

Claim 1, in the line following formula I, insert --and-- before "a".

Claim 1, correct the second formula to read as follows:

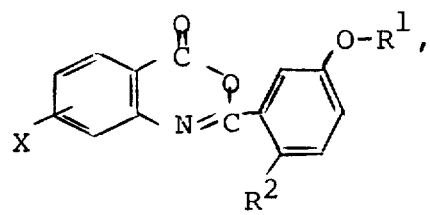

II

Signed and Sealed this

Sixteenth Day of August 1983

[SEAL]

Attest:

GERALD J. MOSSINGHOFF

Attesting Officer      Commissioner of Patents and Trademarks